United States Patent
Nakao (10) Patent No.: US 8,206,401 B2
(45) Date of Patent: *Jun. 26, 2012

(54) ENDOSCOPE CUTTING AND RETRIEVING SNARE INSTRUMENT

(75) Inventor: Naomi L. Nakao, New York, NY (US)

(73) Assignee: Granit Medical Innovation LLC, New York, NY (US)

(*) Notice: Subject to any disclaimer, the term of this patent is extended or adjusted under 35 U.S.C. 154(b) by 1340 days.

This patent is subject to a terminal disclaimer.

(21) Appl. No.: 11/182,543

(22) Filed: Jul. 15, 2005

(65) Prior Publication Data

US 2007/0016224 A1    Jan. 18, 2007

(51) Int. Cl.
*A61B 17/26* (2006.01)

(52) U.S. Cl. .................. 606/113; 606/114; 606/127

(58) Field of Classification Search .................. 606/113, 606/114, 127, 110, 128, 200, 170; 601/4
See application file for complete search history.

(56) References Cited

U.S. PATENT DOCUMENTS

| | | |
|---|---|---|
| 5,234,439 A | 8/1993 | Wilk et al. |
| 5,279,539 A | 1/1994 | Bohan et al. |
| 5,352,184 A | 10/1994 | Goldberg et al. |
| 5,376,094 A * | 12/1994 | Kline ............................ 606/113 |
| 5,643,283 A | 7/1997 | Younker |
| 5,741,271 A * | 4/1998 | Nakao et al. .................. 606/114 |
| 5,759,187 A | 6/1998 | Nakao et al. |
| 5,782,840 A * | 7/1998 | Nakao ............................ 606/114 |
| 5,906,621 A | 5/1999 | Secrest et al. |
| 5,997,547 A | 12/1999 | Nakao et al. |
| 6,171,315 B1 | 1/2001 | Chu et al. |
| 6,350,266 B1 * | 2/2002 | White et al. .................. 606/114 |
| 2003/0004538 A1 | 1/2003 | Secrest et al. |
| 2003/0018355 A1 * | 1/2003 | Goto et al. .................... 606/200 |
| 2003/0120281 A1 * | 6/2003 | Bates et al. .................... 606/114 |
| 2003/0212389 A1 * | 11/2003 | Durgin et al. ................... 606/21 |
| 2006/0052798 A1 * | 3/2006 | Kanamaru ..................... 606/113 |
| 2007/0016225 A1 * | 1/2007 | Nakao ........................... 606/114 |

* cited by examiner

*Primary Examiner* — Tuan Nguyen
*Assistant Examiner* — Thomas McEvoy
(74) *Attorney, Agent, or Firm* — R. Neil Sudol; Coleman Sudol Sapone, P.C.

(57) ABSTRACT

An endoscopic cutting and retrieval instrument includes an elongate electrically conductive wire and an inner loop and an outer loop both connected to a distal end of the wire. The inner loop and the outer loop have a common proximal loop portion and different distal loop portions. The distal loop portion of the outer loop is longer than the distal loop portion of the inner loop so that the outer loop is larger than the inner loop. A net attached to the outer loop forms a retrieval basket for capturing severed polyps and other tissues masses.

1 Claim, 9 Drawing Sheets

ENDOSCOPE CUTTING AND RETRIEVING SNARE INSTRUMENT

BACKGROUND OF THE INVENTION

This invention relates to a surgical instrument assembly for use in removing and retrieving selected tissues from internal body cavities of a patient. This invention more specifically relates to an instrument assembly for use in snare operations. The invention is particularly useful in the removal of polyps, for example, from the colon of a patient during an endoscopic procedure.

In a conventional endoscopic snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope. The use of a forceps generally prevents one from removing more than a biopsy sample from the patient. The forceps naturally tears off a tissue sample from a severed polyp, leaving the main body of the polyp in the patient. In using suction, a vacuum is applied via a suction channel of the endoscope. The use of suction has the drawback of frequently preventing visual inspection of the patient's internal tissues during withdrawal of the endoscope. The polyp or other tissue mass is drawn against the front end of the endoscope, thus obscuring the light source and the observation lens.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In some cases, the endoscope must be removed without the polyp and the patient given an enema in an attempt to flush out the polyp from the colon.

Furthermore, there are numerous cases where a severed polyp is never recovered. Sometimes, the polyp is macerated during the retrieval attempt. In all such cases, the pathologist is unable to determine whether the polyp contains carcinoma in situ (localized to the mucosal surface) or infiltrative carcinoma (spread beyond the muscularis mucosa, a deeper layer of the polyp). The patient must then undergo a colon resection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. No. 5,201,740 to Nakao et al. provides a solution to the above-described problems in polyp removal. Pursuant to the disclosure of that patent, snare cauterization operations are performed with a surgical instrument assembly comprising a tubular sheath member carrying a metallic cauterization loop and a metal wire operatively connected to the loop, the wire passing longitudinally through the sheath. An electrical supply is operatively connectable to the wire, while a flexible web member is connected to the loop to form a capture pocket, the loop defining a mouth opening of the pocket. During use of the snare cauterization loop, the web member is passed over and substantially surrounds a polyp. The pocket captures the polyp at the same time that the cauterization loop is energized to effectuate a severing of the polyp. This cauterization snare assembly with attached pocket is a substantial advance over conventional polyp removal techniques.

Other improvements are disclosed in U.S. Pat. Nos. 5,190,542, 5,374,273, 5,234,439, 5,782,840, 5,741,271, 5,336,227, 5,486,182, 5,759,187, and U.S. Patent Publication No. 20050085808 all patents to N. Nakao et al.

OBJECTS OF THE INVENTION

An object of the present invention is to provide an improved instrument assembly for the removal of polyps and other organic tissue parts from patients, particularly an instrument assembly useful for resecting and retrieving multiple polyps from a patient's colon.

Another particular object of the present invention is to provide such an instrument assembly which is simple to manufacture and therefore inexpensive.

A further particular object of the present invention is to provide such an instrument assembly which is easy to use.

Yet another object of the present invention is to provide an associated method for the removal of tissue samples from a patient.

These and other objects of the present invention will be apparent from the descriptions and drawings herein. It is to be noted that each object is attained by one or more embodiments of the invention. No single embodiment, however, need attain all objects stated implied herein.

SUMMARY OF THE INVENTION

A surgical instrument in accordance with the present invention comprises an elongate slider member and an inner loop and an outer loop both connected to a distal end of the slider member. The inner loop and the outer loop have a common proximal loop portion and different distal loop portions. The distal loop portion of the outer loop is longer than the distal loop portion of the inner loop so that the outer loop is larger than the inner loop.

The word "proximal" is used herein to designate relative proximity to the user of the surgical instrument, for example, a surgeon or endoscopist. Concomitantly, the word "distal" is used herein to relative remoteness from the user of the surgical instrument. Thus, an element that is distal relative to another element is located on a side of the instrument that is farther from the user or handle end of the instrument.

Pursuant to further features of the present invention, the inner loop and the outer loop are at least partially coplanar with one another (at least along the proximal side), and the distal loop portions are attached to one another on their proximal side, i.e., the side facing the elongate slider member. More particularly, the distal loop portions are soldered, glued, ultrasonically welded, coupled by laser, or otherwise bonded to one another on their proximal sides. In accordance with a more specific feature of the present invention, one of the distal loop portions is continuous and integrally formed with the proximal loop portion to form a main loop, while the other distal loop portion comprises a separate section soldered, glued, ultrasonically welded, coupled by laser, or otherwise bonded to the main loop along opposite sections thereof. Where the main loop includes a nose opposite the elongate slider member and two sections extending between the slider member and the nose, the other distal loop portion is soldered, glued, ultrasonically welded, coupled by laser, or otherwise bonded to the opposite sections of the main loop preferably at points equidistant from the nose.

The main loop, that is, the loop that includes the proximal loop portion as an integral part, may be the inner loop or the outer loop. Where the main loop is the inner loop, the distal loop portion of the outer loop is soldered or otherwise bonded to the main loop. Conversely, where the main loop is the outer loop, the distal loop portion of the inner loop is soldered or otherwise bonded to the main loop.

In a preferred embodiment of the invention, a pouch is attached at least to a larger of the distal loop portions, with the outer loop partially defining a mouth of the pouch. In this embodiment of the invention, the distal portion of the inner loop may diverge out of the plane of the outer loop, in a direction away from the pouch. Typically, the device further includes an elongate tubular introducer member or sheath such as a catheter, into which the loop and pouch may be drawn. As the pouch is drawn into the catheter, the distal portion of the inner loop is drawn towards the plane of the outer loop.

The resulting device functions as a cutting snare combined with a retrieval basket. In particular, the inner loop functions as a cutting snare while the outer loop with the attached pouch functions as the retrieval basket. The inner loop may be a thin braided cable or a monofilament wire, so that polypectomies and other cutting operations may be performed cold, i.e., without cautery. Alternatively, the cutting snare may be made of electrically conductive material for purposes of cauterizing tissues during a cutting operation. In that case, the slider member is or includes an electrically conductive element. Because more current is conducted through the inner distal loop portion than the outer distal loop portion during a tissue severing and cauterization procedure, the attachment of the netting to the outer loop is likely to remain intact, thereby enabling the harvesting of multiple polyps from a patient with the same instrument.

Where the instrument further comprises a tubular member, the slider member being slidably disposed at least partially inside the tubular member, the instrument may also comprise one or more tethers attached to the pouch on a proximal side thereof. The one or more tethers extend into the tubular member and are connected thereto, inside the lumen of the tubular member.

Pursuant to a feature of the present invention, at least one tether is fastened to the tubular member at a location spaced by a distance from a distal tip of the tubular member, and that tether has a length from the location to the pouch that is greater than the distance between the location and the tip of the tubular member. There may be a plurality of such tethers that have such a length longer that the distance between the location and the tip of the tubular member. In addition, a most proximal portion of the pouch may itself extend into the tubular member. In that case an additional tether may be fastened to the most proximal portion of the pouch, the additional tether having a length from the location to the pouch that is less than the distance between the location and the tip of the tubular member.

A surgical instrument comprises, in accordance with the present invention, an elongate slider member, a first loop portion connected along a middle region to the elongate slider member, the first loop portion being concave in a direction facing away from the slider member and convex on a side facing the slider member. The first loop portion has a pair of first arms each continuous and contiguous with the middle region and extending away from the middle region and the slider member and from each other. A second loop portion concave in a direction facing the slider member and convex on a side facing away from the slider member has a pair of second arms each continuous and contiguous with respective ones of the first arms so that the second loop portion forms a continuous and closed inner loop with the first loop portion. A third loop portion also concave in a direction facing the slider member and convex on a side facing way from the slider member has a pair of third arms each continuous and contiguous with respective ones of the first arms so that the third loop portion forms a continuous and closed outer loop with the first loop portion. The outer loop is larger than the inner loop.

A netting is preferably attached at least to the third loop portion to form a pouch with the outer loop partially defining a mouth of the pouch.

Where the second loop portion or the third loop portion is integral with the first loop portion, the arms of the other of the second loop portion and the third loop portion are bonded to the first arms. This bond may be implemented via a soldered coupling.

DETAILED DESCRIPTION

Figure 1:
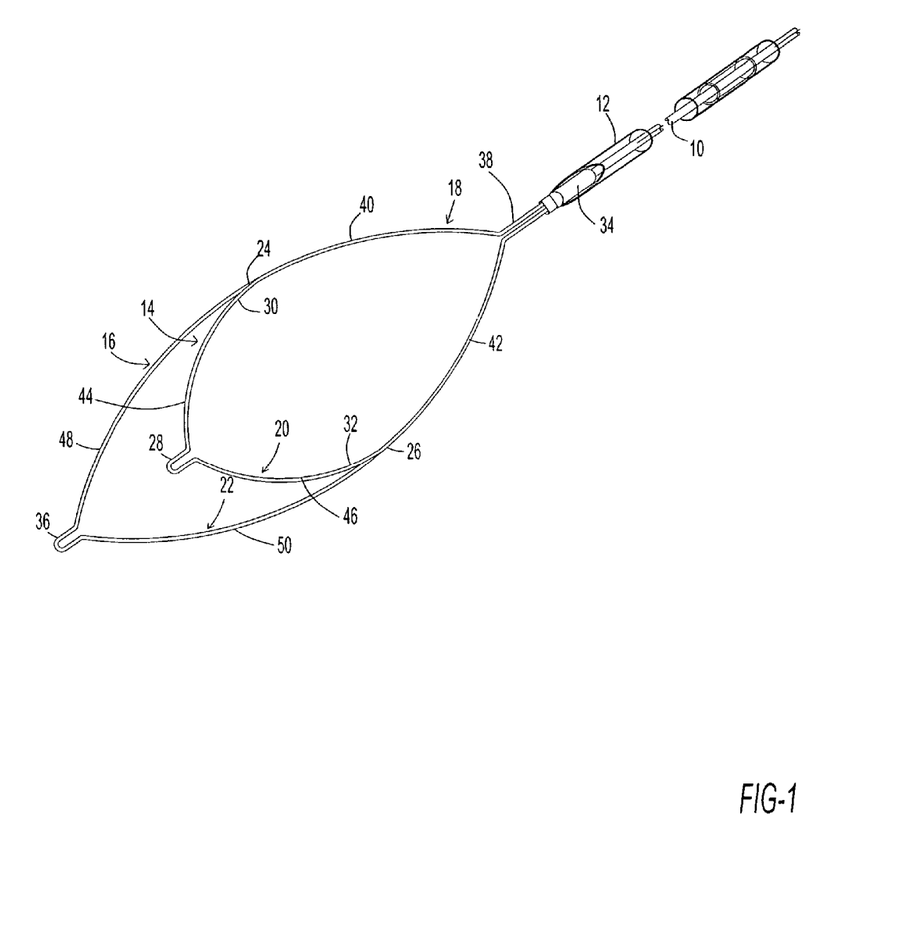
FIG. 1 is a schematic perspective view of a two-tiered cutting loop in accordance with the present invention.

As depicted in FIG. 1, a surgical instrument for use in an endoscopic tissue resection procedure comprises an elongate electrically conductive slider member or pusher wire 10 movably extending through a tubular introducer member 12 such as a catheter. The catheter is dimensioned to fit down the biopsy channel of a flexible endoscope. The instrument of FIG. 1 additionally comprises an inner loop 14 and an outer loop 16 (collectively, an end effector) both operatively connected to a distal end of wire 10. Inner loop 14 and the outer loop 16 have a common proximal loop portion 18 and different distal loop portions 20 and 22. The distal loop portion 22 of outer loop 16 is longer than the distal loop portion 20 of inner loop 14 with the result that the outer loop is larger than the inner loop. Inner loop 14 and distal loop portion 22 of outer loop 16 each have a width, the largest width of distal loop portion 22 of outer loop 16 being at least as large as the largest width of inner loop 14.

At its proximal end (not shown), wire 10 is operatively connectable to a voltage source (not shown) for purposes of conducting current through inner loop 14. Distal loop portion 22 of outer loop 16 is preferably provided with a coating of electrically insulating material such as heat-shrunk polytetrafluoroethylene, so that current is not conducted through distal loop portion 22 in the event of accidental contact with organic tissues during an endoscopic resection procedure.

Inner loop 14 and outer loop 16 are coplanar with one another at least along their proximal sides. Distal loop portions 20 and 22 are soldered, glued, ultrasonically welded, laser welded or otherwise attached to one another at junctions 24 and 26, on their proximal side.

Distal loop portion 20 of inner loop 14 is continuous and integrally formed with proximal loop portion 18 so that inner loop 14 may be viewed as the main loop. Inner loop has a nose 28 at a distal end and a pair of mirror image wire sections or segments 30 and 32 extending between the nose at the distal side and a crimping connector 34 at the proximal side. Distal loop portion 22 of outer loop 16 comprises a separate wire section soldered, glued, ultrasonically welded, coupled by laser, or otherwise attached to inner loop 14 along opposite sections 30 and 32 thereof. Distal loop portion 22 itself has a nose 36 generally aligned with nose 28 and crimping connector 34. Distal loop portion 22 of outer loop 16 is soldered, glued, ultrasonically welded, laser welded or otherwise attached to the opposite sections 30 and 32 of inner loop 14 preferably at points equidistant from nose 28 (and also equidistant from connector 34). Noses 28 and 36 each take the form of a U-shaped bend having two arms spaced a fixed distance from one another where that distance renders the nose smaller (narrower) than the inner diameter of the tubular member 12.

Proximal loop portion 18 is connected along a middle region by a pair of linear parallel connector sections 38 fixed relative to one another and to wire 10 by means of connector 34. Proximal loop portion 18 is arcuate or curved, concave in a direction facing away from wire 10 and convex on a side facing the wire, and forms a portion of an oval loop shape. Proximal loop portion 18 has a pair of first arms 40 and 42 each continuous and contiguous with a respective one of the middle region connector sections 38 and extending away in a distal direction from the middle region, wire 10 and at an ever increasing distance away from each other so that distal ends of the arms are spaced from one another by a distance substantially larger (many times larger) than the inner diameter of the tubular member 12. Distal loop portion 20 of inner loop 14 is concave in a direction facing wire 10 and convex on a side facing away from the wire. Distal loop portion 20 has a pair of arms 44 and 46 continuous and contiguous with arms 40 and 42 of proximal loop portion 18 so that distal loop portion 20 forms inner loop 14 with proximal loop portion 18. Inner loop 14 and outer loop 16 together form an end-effector having a collapsed configuration inside tubular member 12 and the illustrated expanded configuration outside tubular member 12, the two loop arms being movable relative to one another so as to reconfigure end-effector from collapsed configuration to expanded configuration.

Distal loop portion 22 of outer loop 16 is also concave in a direction facing wire 10 and convex on a side facing away from the wire. Distal loop portion 22 has a pair of arms 48 and 50 each continuous and contiguous with respective arms 42 and 44 of proximal loop portion 18 so that the outer distal loop portion 22 together with proximal loop portion 18 forms outer loop 16 as a continuous and closed loop. Arms 48 and 50 are connected to nose 36 at an angle (not 180°) so that arms 42 and 44 extending in on-parallel relation to one another in a deployed or expanded configuration of the dual-loop end effector.

Figure 2:
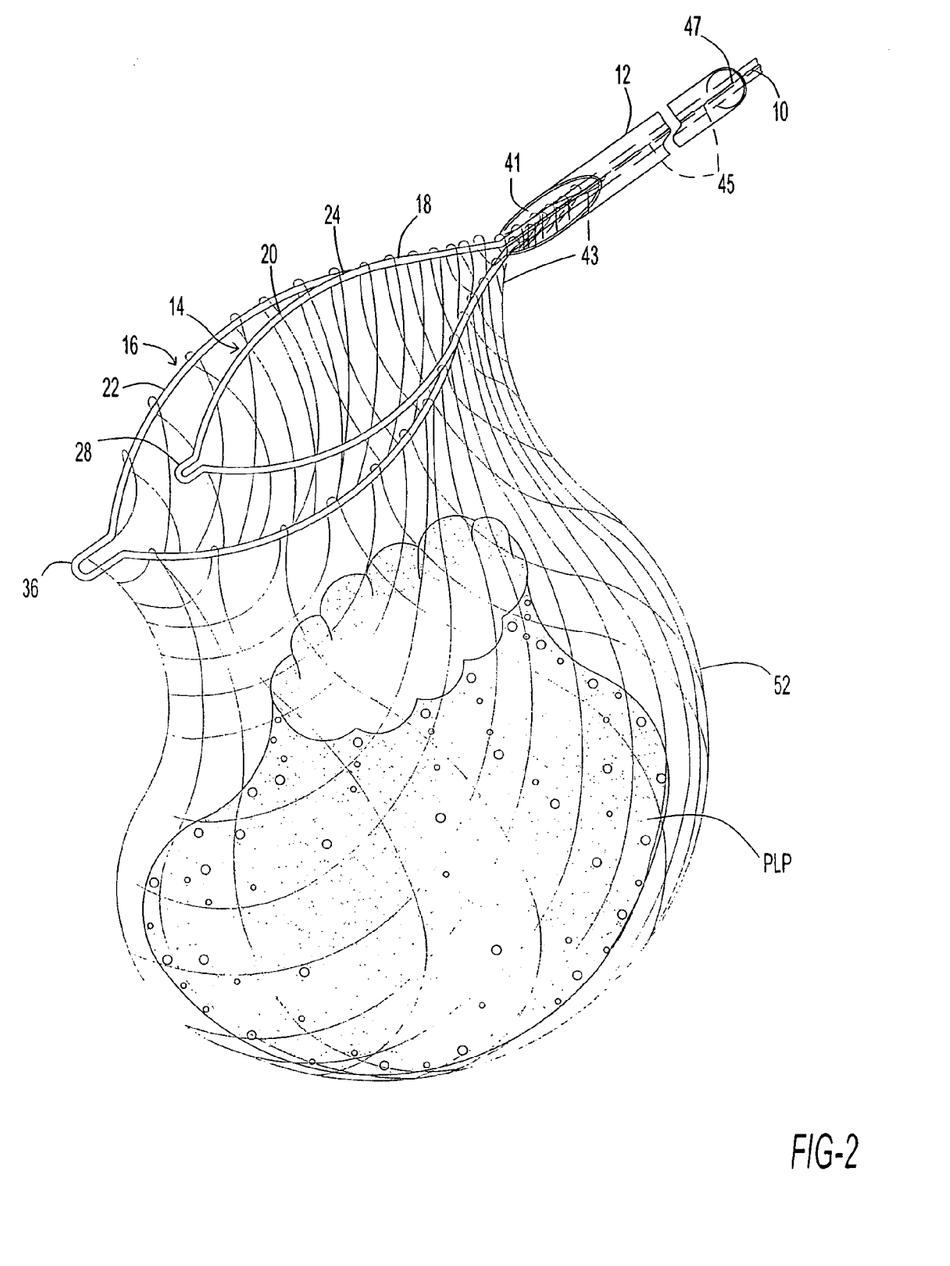
FIG. 2 is a schematic perspective view of the cutting loop of FIG. 1, with the addition of a retrieval net or pouch, thus forming a cutting and retrieval snare instrument.

As illustrated in FIG. 2, outer loop 16 may be provided with a netting or net element 52 that defines a pouch or tissue capture pocket. More specifically, net element 52 is attached to proximal loop portion 18 and outer distal loop portion 22 to form a pouch with outer loop 16 defining a mouth of the pouch. In the device or instrument of FIG. 2, inner loop 14 functions as a cauterization snare while outer loop 16 functions as a retrieval basket. Because current is conducted through inner distal loop portion 20 rather than outer distal loop portion 22 during a tissue severing and cauterization procedure, net element 52 will remain attached to outer loop 16 to facilitate the harvesting of multiple polyps from a patient with the same instrument.

Net element 52 may be slidably attached to outer loop 16 at least along a proximal side thereof. Slidability facilitates repeated withdrawal and extension of loops 14 and 16 by enabling net element 52 to remain outside tubular member 12 during a retraction stroke of wire 10. The net bunches at a distally located mouth 41 of tubular member 12 during a generally partially retraction or withdrawal of loops 14 and 16 into the tubular member. Preferably, net element 52 is fixed to outer loop 16 at a distal point, for example, along nose 36, to prevent the displacement of the net element to one side or the other of the outer loop 16. Fixation may be accomplished by any suitable method, including a clamp, a ringlet, or a glob of biocompatible adhesive.

Particularly in the case that net element 52 is slidably secured to outer loop 16 along at least a proximal portion thereof, net element 52 includes a proximal end portion 43 that extends through mouth 41 into tubular member 12. Portion 43 remains in part inside tubular member at all times during a snare retrieval procedure. One or more tether lines 45 are attached on one side to proximal net portion 43 and are fastened on an opposite side the tubular member 12 at one or more anchor points 47. Each tether line 45 necessarily has an effective length that is significantly less than the distance between anchor point 47 and mouth opening 41 at the free end or distal tip of tubular member 12. Tether 41 exerts a restraining influence on net element 52 via proximal net portion 43, thereby ensuring that net element 43 extends essentially fully around outer loop 16 upon a complete ejection of loops 14 and 16 from tubular member 12. Anchor point 47 and the length of tether 45 are selected to enable a complete retraction of loops 14 and 16 and net element 52 into tubular member 12 during insertion into the working or biopsy channel of the endoscope.

Figure 3:
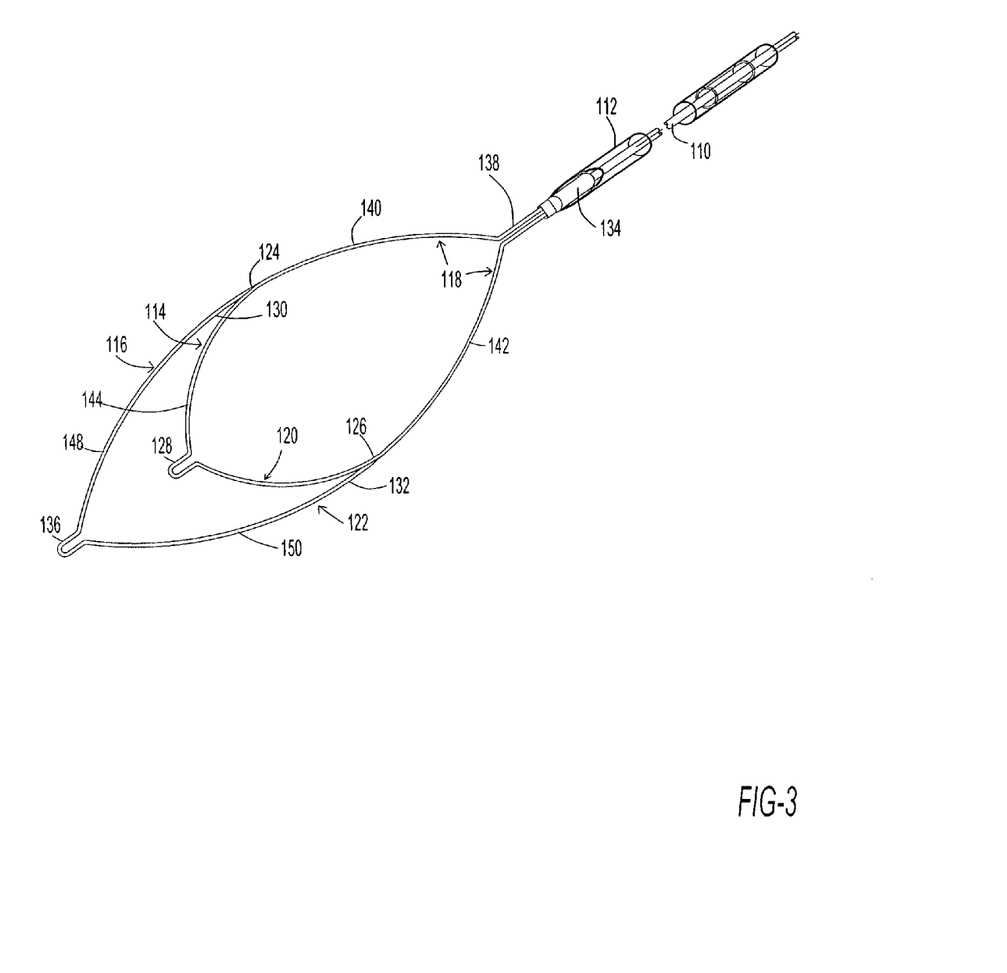
FIG. 3 is a schematic perspective view of another embodiment of a two-tiered cutting loop in accordance with the present invention.

As illustrated in FIG. 3, a modified surgical instrument for use in an endoscopic tissue resection procedure comprises an elongate electrically conductive wire 110 extending through a tubular member 112 with an outer diameter (not designated) smaller than the diameter of an endoscope biopsy channel.

The distal end of wire 110 is provided an inner loop 114 and an outer loop 116 which have a common proximal loop portion 118 and different distal loop portions 120 and 122. Outer distal loop portion 122 is longer than inner distal loop portion 120 so that outer loop 116 is larger than inner loop 114.

At its proximal end (not shown), wire 110 is operatively connectable to an electrical power supply (not shown) for purposes of applying a voltage across inner loop 114. Distal loop portion 122 of outer loop 116 is preferably provided with a coating of electrically insulating material such as heat-shrunk polytetrafluorethylene, so that current is not conducted through distal loop portion 122 during an endoscopic resection procedure.

Inner loop 114 and outer loop 116 are coplanar with one another along proximal loop portion 118. Inner and outer distal loop portions 120 and 122 are soldered, glued, ultrasonically welded, laser welded or otherwise attached to one another at junctions or joints 124 and 126, on their proximal side.

Outer distal loop portion 122 is continuous and integrally formed with proximal loop portion 118 so that outer loop 116 may be viewed as the main loop. Outer loop 116 has a nose 128 at a distal end and a pair of mirror image wire sections or segments 130 and 132 extending between the nose at the distal side and a crimping connector 134 at the proximal side. Distal loop portion 120 of inner loop 114 comprises a separate wire section soldered, glued, ultrasonically welded, laser welded or otherwise attached to outer loop 116 along opposite sections 130 and 132 thereof. Distal loop portion 120 itself has a nose 136 generally aligned with nose 128 and crimping connector 134. Distal loop portion 120 of inner loop 114 is soldered, glued, ultrasonically welded, laser welded or otherwise attached to the opposite sections 130 and 132 of outer loop 116 preferably at points equidistant from nose 128 (and also equidistant from connector 134).

Proximal loop portion 118 is connected along a middle region 138 to wire 110 by means of connector 134. Proximal loop portion 118 is concave in a direction facing away from wire 110 and convex on a side facing the wire. Proximal loop portion 118 has a pair of first arms 140 and 142 each continuous and contiguous with the middle region 138 and extending away from the middle region, wire 10 and from each other. Distal loop portion 120 of inner loop 114 is concave in a direction facing wire 110 and convex on a side facing away from the wire. Distal loop portion 120 has a pair of arms 144 and 146 continuous and contiguous with arms 140 and 142 of proximal loop portion 118 so that distal loop portion 120 together with proximal loop portion 118 forms inner loop 114. Distal loop portion 122 of outer loop 116 is also concave in a direction facing wire 110 and convex on a side facing away from the wire. Distal loop portion 122 has a pair of arms 148 and 150 each continuous and contiguous with respective arms 142 and 144 of proximal loop portion 118 so that the outer distal loop portion 122 together with proximal loop portion 118 forms outer loop 116 as a continuous and closed loop.

Figure 4:
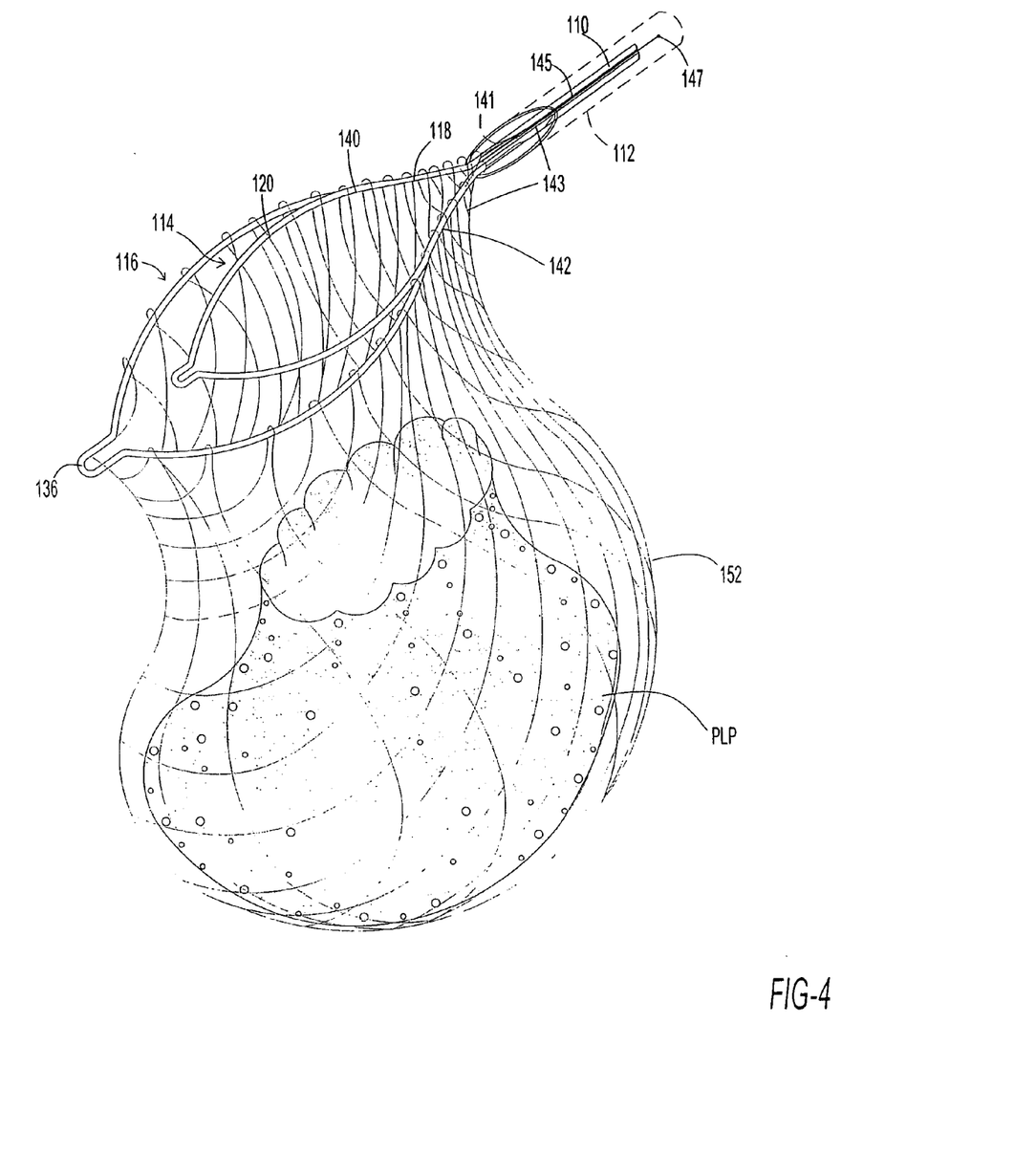
FIG. 4 is a schematic perspective view of the cutting loop of FIG. 3, with the addition of a retrieval net or pouch, thus forming a cutting and retrieval snare instrument.

As illustrated in FIG. 4, outer loop 116 may be provided with a netting or net element 152 that defines a pouch or tissue capture pocket. More specifically, net element 152 is attached to proximal loop portion 118 and outer distal loop portion 122 to form a pouch with outer loop 116 defining a mouth of the pouch. In the device or instrument of FIG. 4, inner loop 114 functions as a cauterization snare while outer loop 116 functions as a retrieval basket. Because current is conducted through inner distal loop portion 120 and not through outer distal loop portion 122 during a tissue severing and cauterization procedure, net element 152 will remain attached to outer loop 116, thereby facilitating the harvesting of multiple polyps from a patient with the same instrument.

Net element 152 may be slidably attached to outer loop 116 at least along a proximal side thereof. Slidability facilitates repeated withdrawal and extension of loops 114 and 116 by enabling net element 152 to remain outside tubular member 112 during a retraction stroke of wire 110. The net bunches at a distally located mouth 141 of tubular member 112 during a generally partially retraction or withdrawal of loops 114 and 116 into the tubular member.

Particularly in the case that net element 152 is slidably secured to outer loop 116 along at least a proximal portion thereof, net element 152 includes a proximal end portion 143 that extends through mouth 141 into tubular member 112. Portion 143 remains in part inside tubular member at all times during a snare retrieval procedure. One or more tether lines 145 are attached on one side to proximal net portion 143 and are fastened on an opposite side the tubular member 112 at one or more anchor points 147. Each tether line 145 necessarily has an effective length that is less than the distance between anchor point 147 and mouth opening 141 at the free end or distal tip of tubular member 112. Tether 141 exerts a restraining influence on net element 152 via proximal net portion 143, thereby ensuring that net element 143 extends essentially fully around outer loop 116 upon a complete ejection of loops 114 and 116 from tubular member 112. Anchor point 147 and the length of tether 45 are selected to enable a complete retraction of loops 114 and 116 and net element 152 into tubular member 112 during insertion into the working channel of the endoscope.

Providing net elements or pouches 52 and 152 with proximal net portions 43 and 143 that extend into the tubular members 12 and 112 and that are connected to tethers 45 and 145 inside the tubular members provides some distinct advantages over tissue retrieval instruments where the net remains substantially completely outside the tubular member during repeated ejection and retraction operations. The fact that tethers 45, 145 are shorter than the distance between the distal tip of the tubular introducer member 12, 112 and attachment points 47, 147 enables proximal net portion 43, 143 to be brought inside tubular member 12, 112. The net 52, 152 is thereby stretched to produce a tauter, flatter net configuration when the snare assembly is fully deployed, while still maintaining the advantage of forming a pouch when withdrawn. A tauter, flatter net configuration particularly in the fully extended position of the net element 52, 152 assists in tissue handling procedures. Visibility is enhanced and loop handling is facilitated.

Figure 5:
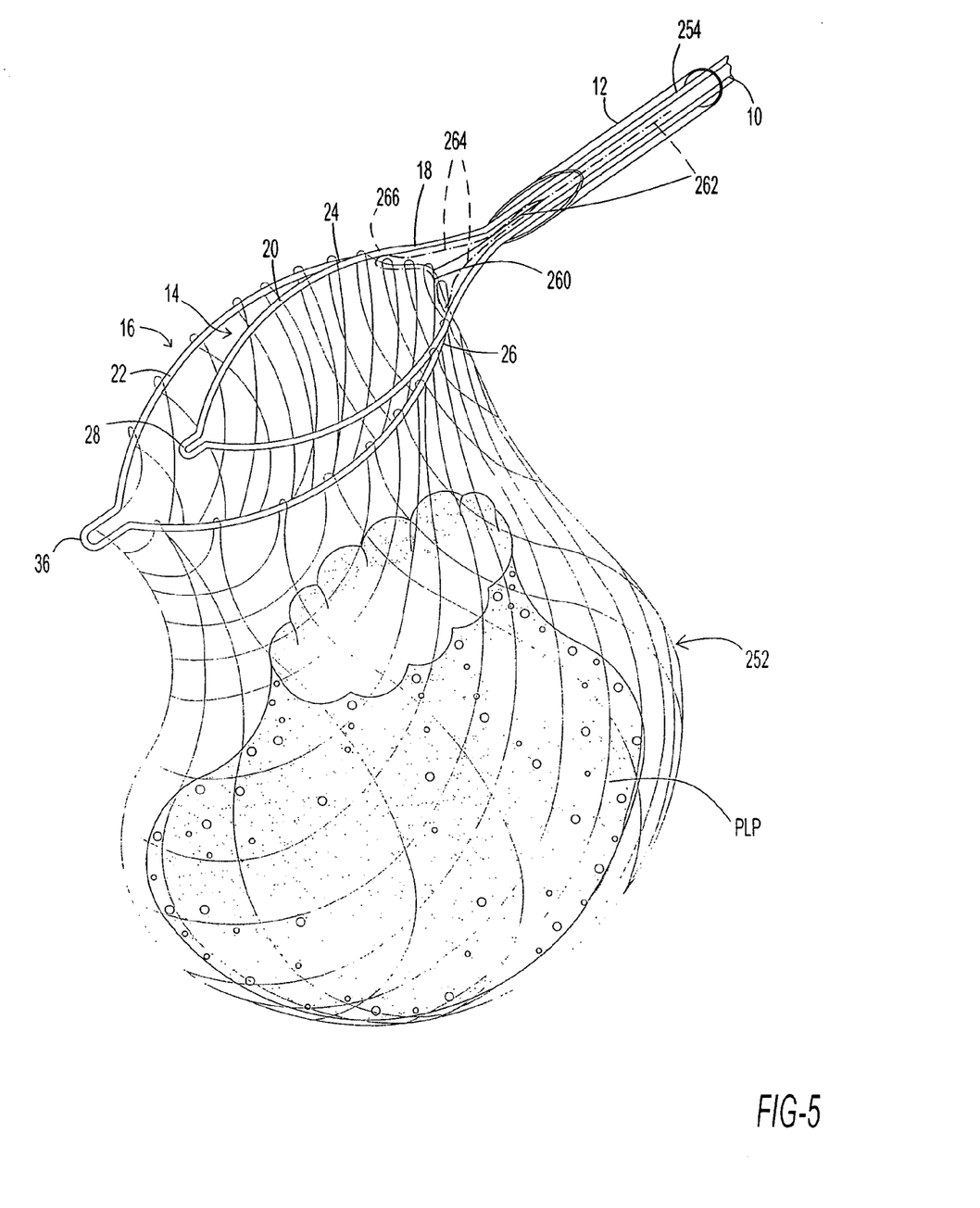
FIG. 5 is a schematic perspective view of a modification of the cutting and retrieval snare instrument of FIG. 2.

FIG. 5 illustrates a modification of the surgical instrument of FIG. 2. Instrument parts in FIG. 5 are designated with the same reference numerals as the same parts in FIG. 2. As depicted in FIG. 5, a pouch 252 made of film or netting material is slidably attached to outer distal loop portion 22 so that the outer loop portion partially defines a mouth (not separately labeled) of the pouch.

Outer loop portion 22 is connected to inner loop portion 20 and to proximal loop portion 18 at junctions or branch points 24 and 26. On a proximal side 258, pouch 252 has a mouth edge or thread 260 that extends between junction or branch point 24 and junction or branch point 26. A tether 262 in the form of a thread is connected at a distal end to the proximal edge or mouth 260 of pouch 252 and extends proximally into tubular member 12 to be connected at a proximal end to tubular member 12 at a point 254 inside the lumen of the tubular member. When the loop assembly, including proximal loop portion 18, inner loop portion 20, and outer loop portion 22, is fully extended in the distal direction, tether 262 pulls edge 260 in the proximal direction to maximize the size or cross-sectional area of the pouch mouth. Plural tethers 264 may be alternatively or additionally provided, tethers 264 being attached to edge 260 at spaced locations therealong, thereby facilitating that the pouch mouth is rounder and wider on the proximal side. Alternatively, a tether 266 may be looped or woven with pouch 252 substantially parallel to or along edge 260. The woven coupling of tether 266 and pouch 252 enhances the reliability of the connection and spreads the forces out over a larger portion of the net. In addition, the woven coupling ensures a greater degree of opening of the pouch, at least along a proximal side thereof.

Tethers 262, 264, 266 necessarily have effective lengths that are significantly greater than the distance between anchor point 254 and the free end or distal tip of tubular member 12.

Tethers 262, 264, 266 serve in part to reopen pouch 252 after the loops 14 and 16 have been retracted inside tubular member 12 during an endoscopic procedure. In other words, tethers 262, 264, 266 serve the additional function of holding the net element when loops 14 and 16 are pushed in the distal direction, thus ensuring that pouch 252 slides relative to the outer loop 16 and has a mouth (not separately labeled) that is open for the capture of a polyp or other tissue mass.

The pouch configuration of FIG. 5 may be used alternatively to net element 152 in the instrument assembly of FIG. 4.

Figure 6:
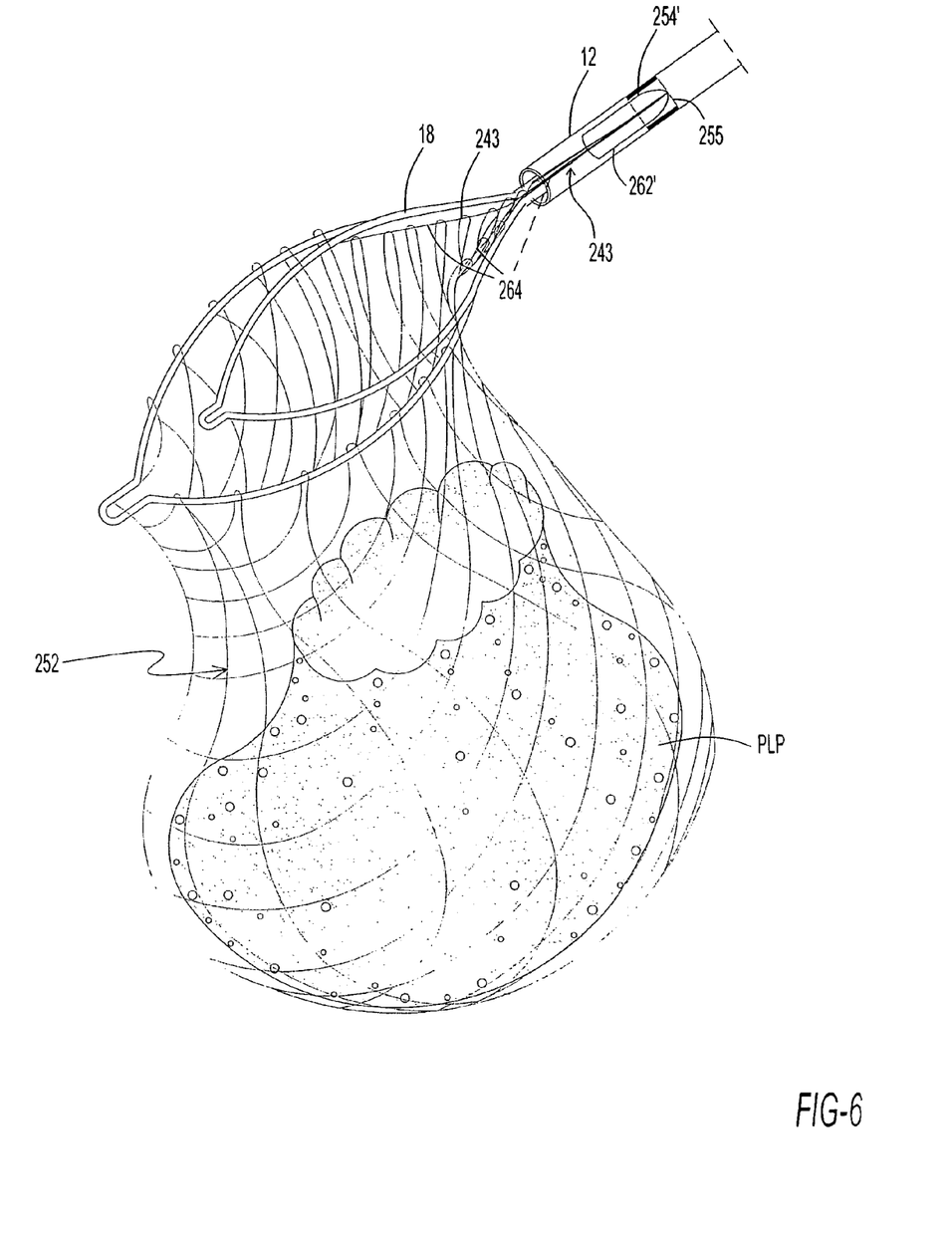
FIG. 6 is a partial schematic perspective view of a cutting and retrieval snare instrument, representing a modification of the instrument of FIG. 5.

As depicted in FIG. 6, the embodiment of FIG. 5 may be modified so that pouch 252 includes a proximal portion 243 that extends into tubular member 12. In that case, a tether loop 262' (replacing tether 262) has an effective length that is less than the distance between an anchor point 254' and the free end or distal tip of tubular member 12. Tethers 262' and 264 are fastened inside (not separately labeled) of tubular member 12 via a metal sleeve 255 that is pressure fit or bonded in some other manner to the tubular member. Tethers 264 in this modified embodiment each extend from a point outside tubular member 12, that is distal to the free end or distal tip of tubular member 12, to anchor point 254' at sleeve 255 and thus retain an effective length that is greater than the distance between anchor point 254' and the free end or distal tip of tubular member 12.

The tether loop 262' as illustrated in FIG. 6 represents a virtual loop, which may be created by knotting either the proximal, or distal ends of the tether, thus creating said loop. Other means of fastening the tether inside the catheter are by bringing its proximal an end through the metal sleeve 255, knotting the two ends together, and then forcing the sleeve up the catheter in the proximal direction to form a pressure fitting of the sleeve against the inner walls of the catheter. The proximal aspects of the tether may also be glued to the sleeve, or to the catheter itself. In some cases, both aspects (proximal and distal) may be knotted. The proximal ends of the tether may be knotted to the netting in one or more points, and/or to the metal pressure fit ring, or another member to be pushed into the catheter for securing said tether in place.

Distal portions 22 and 122 of loops 16 and 116 may be provided with an electrically insulating coating such as a heat-shrink polytetrafluoroethylene layer. However, the insulating coating on distal portions 22 and 122 of outer loops 16 and 116 is merely a precautionary measure, provided in the event of accidental contact with organic tissues. In the absence of such accidental contact, current will never be conducted via distal loop portions 22 and 122 of outer loops 16 and 116. In contrast, distal portions 20 and 120 of loops 14 and 114 are naked metal, permitting the conducting of current upon contact of the distal portions 20 and 120 with organic tissues inside a patient.

Figure 7:
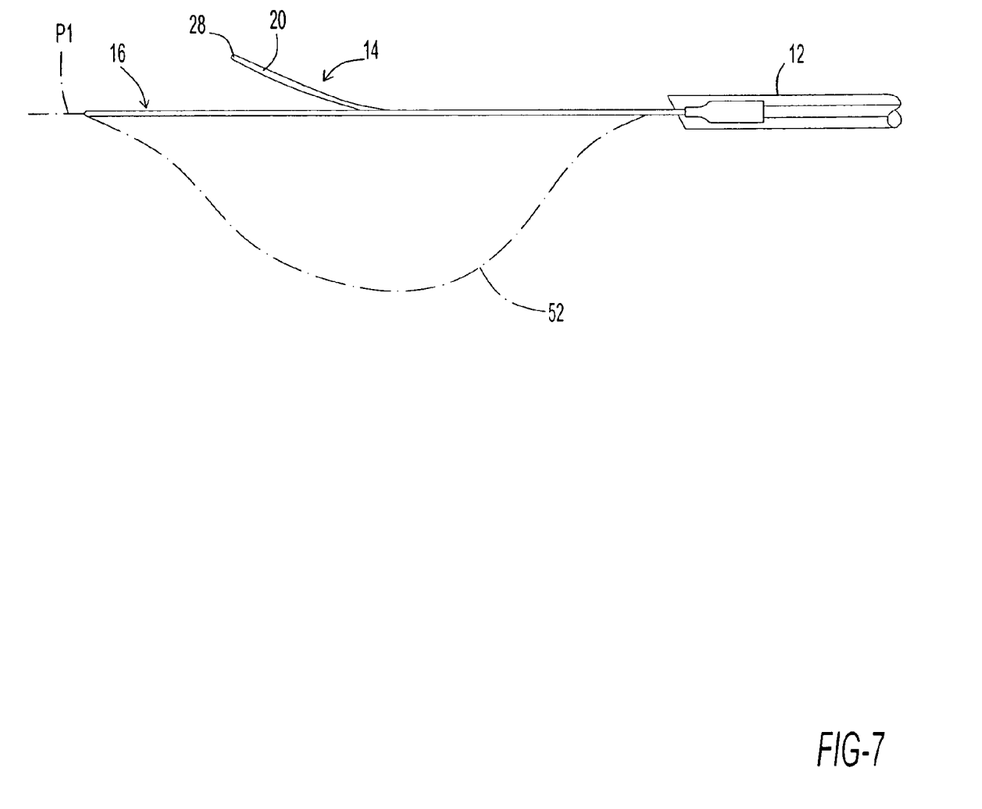
FIG. 7 is a schematic side elevational view of a modified embodiment of a cutting and retrieving instrument in accordance with the present invention.

As depicted in FIG. 7, distal portion 20 (or 120) of inner loop 14 (or 114) may diverge out of the plane P1 of outer loop 16 (or 116), in a direction away from the pouch 52 (or 152). This configuration reduces the likelihood that pouches 52 and 152 will become snagged on the noses 28 and 128 of inner loops 14 and 114, particularly during a deployment process. As the pouches 52 and 152 are drawn into the catheters 12 and 112, the distal portions 20 and 120 of the inner loops 14 and 114 are drawn towards the plane P1 of the outer loops 16 and 116. Loops 14 and 114, particularly distal loop portions 20 and 120, may be made of a stainless steel or other material that has an inherent spring bias tending to reform the distal loop portions into a diverging configuration even upon repeated ejections of the loops 14, 16, 114, 116 from the tubular catheter members 12, 112.

Figure 8:
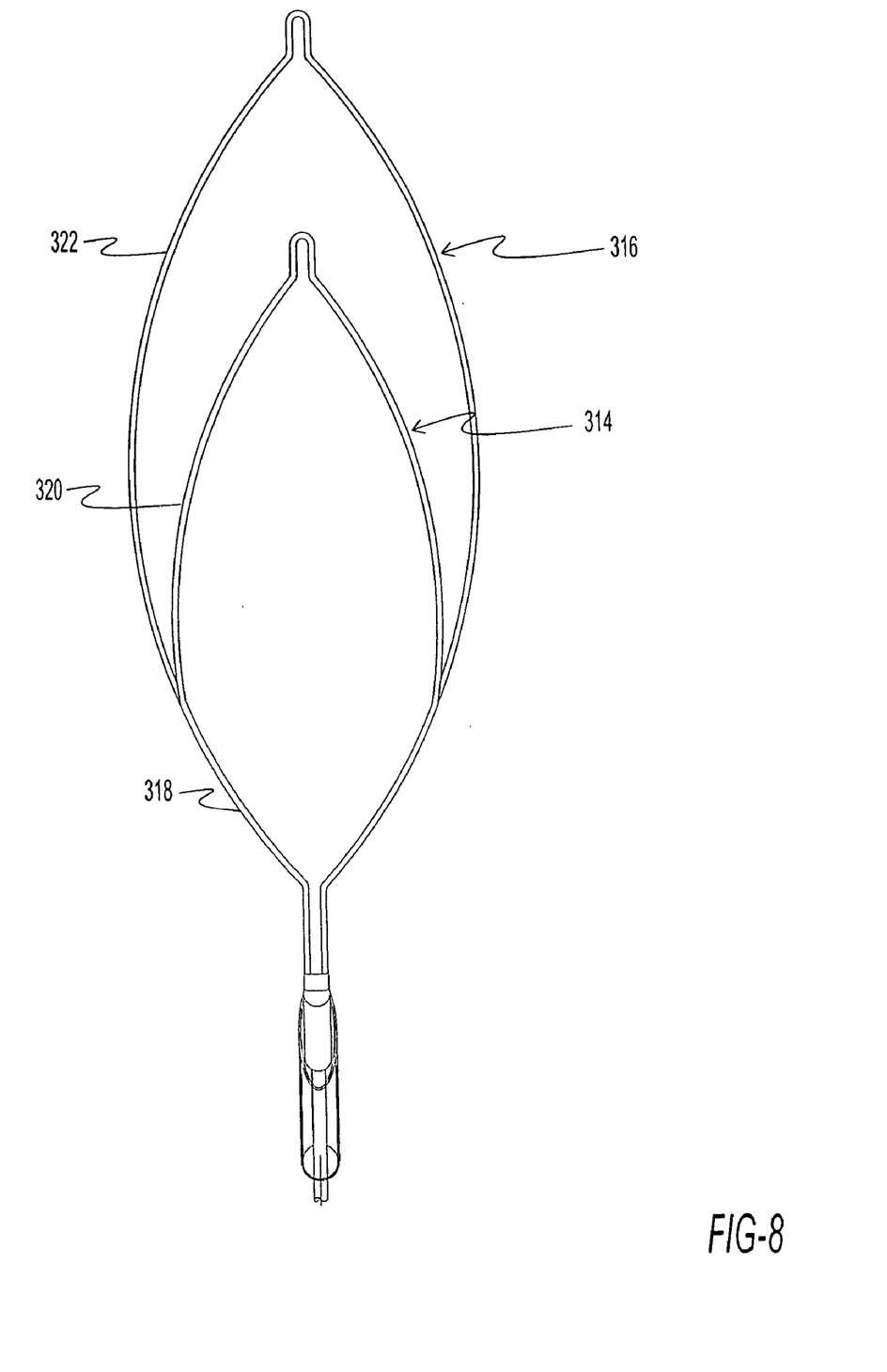
FIG. 8 is a schematic top plan view of another modified embodiment of a cutting and retrieving instrument in accordance with the present invention.
Figure 9:
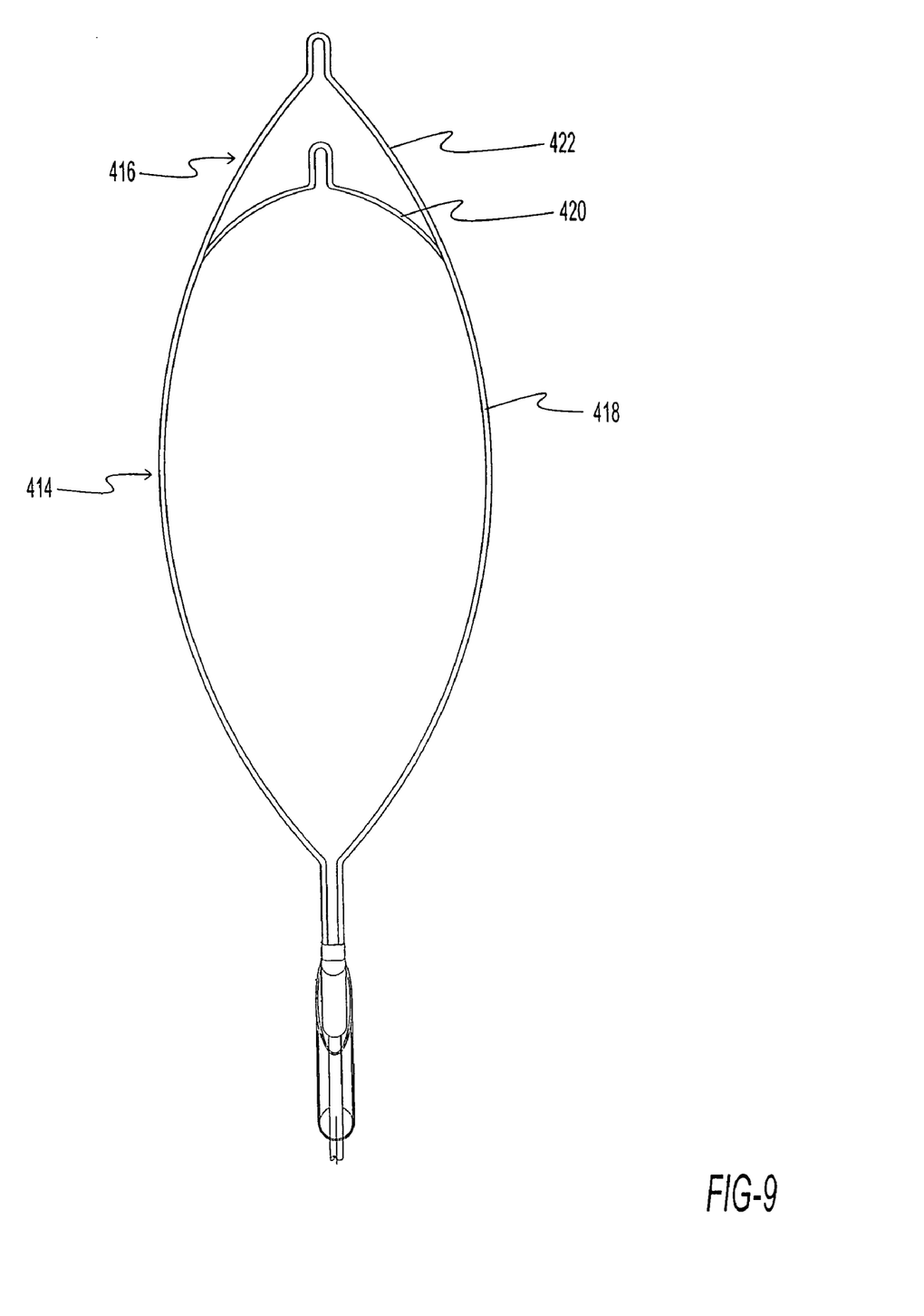
FIG. 9 is a schematic top plan view of yet another modified embodiment of a cutting and retrieving instrument in accordance with the present invention.

FIGS. 8 and 9 depict two extremes of the multi-tier cutting (and retrieving) snare instruments disclosed herein, with respect to the locations of junctions or joints 24, 26, 124, 126 and concomitantly the relative sizes of proximal loop portion 18, 188, on the one hand, and distal loop potions 20, 22, 120, 122, on the other hand. FIG. 8 schematically shows a cutting and retrieving instrument having an inner loop 314 and an outer loop 316 having a common proximal loop portion 318 and separate distal loop portions 320 and 322. Proximal loop portion 318 is much smaller than distal loop portions 320 and 322. In this embodiment a net or pouch (not shown) can be slidably attached to distal loop portion 322 so as to be slidable along the major portion of outer loop 316. The cutting and retrieving instrument of FIG. 8 is an extreme version of the instrument of FIG. 5.

FIG. 9 schematically shows a cutting and retrieving instrument having an inner loop 414 and an outer loop 416 having a common proximal loop portion 418 and separate distal loop portions 420 and 422. Proximal loop portion 418 is much larger than distal loop portions 420 and 422. In this embodiment a net or pouch (not shown) is fixedly attached to outer loop 416 and is therefore not slidable therealong. The net (52, 152) is made sufficiently large and with fine threads so that a large portion of the net remains outside the tubular member (12, 112) when the snare loops are retracted back inside the tubular member, for instance, for purposes of severing a polyp. Net element 52, 152 may be fixed along its entire mouth opening to the respective outer loop 16, 116 in at lest some intermediate configurations between that of FIG. 8 and that of FIG. 9. Tethers as described hereinabove are omitted in the case of net fixation to outer loop 16 or 116.

Although the invention has been described in terms of particular embodiments and applications, one of ordinary skill in the art, in light of this teaching, can generate additional embodiments and modifications without departing from the spirit of or exceeding the scope of the claimed invention. For example, the attachment of the loop sections to one another may be accomplished by a method other than bonding. For instance, the attachment may be effectuated by a clamp or crimping element or by a fine wire wound overlapping loop portions.

In addition, inner loops 14 and 114 may be used in a cold cutting operation, that is, without cautery. In that case inner loops 14 and 114 may be monofilament wires or thin braided cables that are used to cut small polyps by simply being drawn through base regions of the polyps. Such a monofilament wire or thin braided cable need not conduct electrical current since cauterization is not necessary where a polyp is so small as to be vascularized by only capillaries, without a dedicated artery. Cutting snares 14 and 114 are electrically energized where larger polyps are to be removed. In such a case, the cauterization will avoid a major gastrointestinal hemorrhage.

Cutting snares 14 and 114 may also be electrically energized where a smaller polyp is to be removed, when the polyp is in a segment of the colon in which the wall is not very thin and where risk of perforation is miniscule. It may be necessary to cauterize a small polyp if this polyp is suspected of neoplasm. The act of cauterization eliminates surrounding and underlying malignant or pre-malignant cells, minimizing the incidence of recurrence.

Accordingly, it is to be understood that the drawings and descriptions herein are proffered by way of example to facilitate comprehension of the invention and should not be construed to limit the scope thereof.

What is claimed is:

1. A surgical instrument used for endoscopic resection and retrieval of internal tissues, comprising:
   a. a tubular member insertable through a biopsy channel of an endoscope, said tubular member having an inner diameter;
   b. an elongate slider member movably extendible through said tubular member;
   c. an end-effector connected to a distal end of said slider member, said end-effector having a collapsed configuration inside said tubular member and an expanded configuration outside said tubular member, said end effector comprising an inner and an outer loop portion, said loop portions having a common proximal loop portion and different distal loop portions, said proximal loop portion comprising two loop arms each connected at a proximal end to a respective connector section and in turn at least indirectly connected to said slider member, the connector sections having a fixed configuration relative to one another, said two loop arms being movable relative to one another so as to reconfigure said end-effector from said collapsed configuration to said expanded configuration, said two loop arms each extending in a distal direction away from the respective connector section and at least in part at an ever increasing distance away from the other of said two loop arms in the expanded configuration of said end-effector so that distal ends of said two loop arms are spaced from one another by a distance substantially larger than said inner diameter;
   d. said inner and outer loop portions each including, at respective distal ends thereof, a nose, each said nose being a substantially U shaped bend wherein two arms of each said U shaped bend remain in a fixed configuration relative to one another;
   e. said end effector further comprising a capture pouch, said pouch being fixedly attached at a distal end thereof to the nose of said outer loop portion, and slidably extendable around at least the distal portion of said outer loop portion; and
   f. at least one tether fastened at one end thereof to said pouch, and anchored at another end thereof to a point inside said tubular member, wherein said tether has a length that is less than the distance between the anchor point inside said tubular member and a mouth opening at a distal end of said tubular member.

* * * * *